United States Patent
Rapp et al.

(10) Patent No.: US 6,224,904 B1
(45) Date of Patent: May 1, 2001

(54) TABLETS CONTAINING A SWEETENING MIXTURE

(75) Inventors: Knut M. Rapp, Offstein; Ingrid Willibald-Ettle, Landau, both of (DE)

(73) Assignee: Sudzucker Aktiengesellschaft (DE)

( * ) Notice: Subject to any disclaimer, the term of this patent is extended or adjusted under 35 U.S.C. 154(b) by 0 days.

(21) Appl. No.: 09/147,903

(22) PCT Filed: Aug. 9, 1997

(86) PCT No.: PCT/EP97/04346

§ 371 Date: May 27, 1999

§ 102(e) Date: May 27, 1999

(87) PCT Pub. No.: WO98/12936

PCT Pub. Date: Apr. 2, 1998

(30) Foreign Application Priority Data

Sep. 25, 1996 (DE) .............................. 196 39 343

(51) Int. Cl.⁷ ..................................... A61K 9/20
(52) U.S. Cl. ................. 424/464; 424/439; 424/440; 424/441; 424/465; 514/777; 514/778; 514/781
(58) Field of Search ................... 424/439, 440, 424/441, 464, 465

(56) References Cited

U.S. PATENT DOCUMENTS 5,578,339 * 11/1996 Kunz et al. ....................... 426/658

FOREIGN PATENT DOCUMENTS

| 3741961 | 4/1989 | (DE) . |
| 0028905 | 5/1981 | (EP) . |
| 0625578 | 11/1994 | (EP) . |
| 94/08560 | 4/1994 | (WO) . |
| 96/09036 | 3/1996 | (WO) . |
| 97/30598 | 8/1997 | (WO) . |

OTHER PUBLICATIONS

T. Dörr, et al., "Beurteiling der Auflösekinetic Oralen Pharmazeutischer Darreichungsformen aus Verschiedenen Sacchariden und Zuckeraustauschstoffen", Bd. 58, Nr. 10, 1996, pp. 947–952.

F.W. Lichtenthalter, et al., "The Preferred Conformations of Glycosylalditols", Liebig's Annalen der Chemie, 1981, pp. 2372–2383.

* cited by examiner

Primary Examiner—James M. Spear
(74) Attorney, Agent, or Firm—Ostrolenk, Faber, Gerb & Soffen, LLP

(57) ABSTRACT

The present invention relates to a compressed formulation containing 1,1-GPS (1-O-α-D-glucopyranosyl-D-sorbitol) or a mixture of sweetening agents composed of 1,1-GPS, 6-0-α-D-glucopyranosyl-D-sorbitol (1,6-GPS) and 1-0-α-D-glucopyranosyl-D-mannitol (1,1 GPM).

19 Claims, 1 Drawing Sheet

KINETICS OF SOLUTION OF THE COMPRESSED FORMULATIONS:

— ISOMALT ᴿ
— 1,1–GPS
— SUCROSE

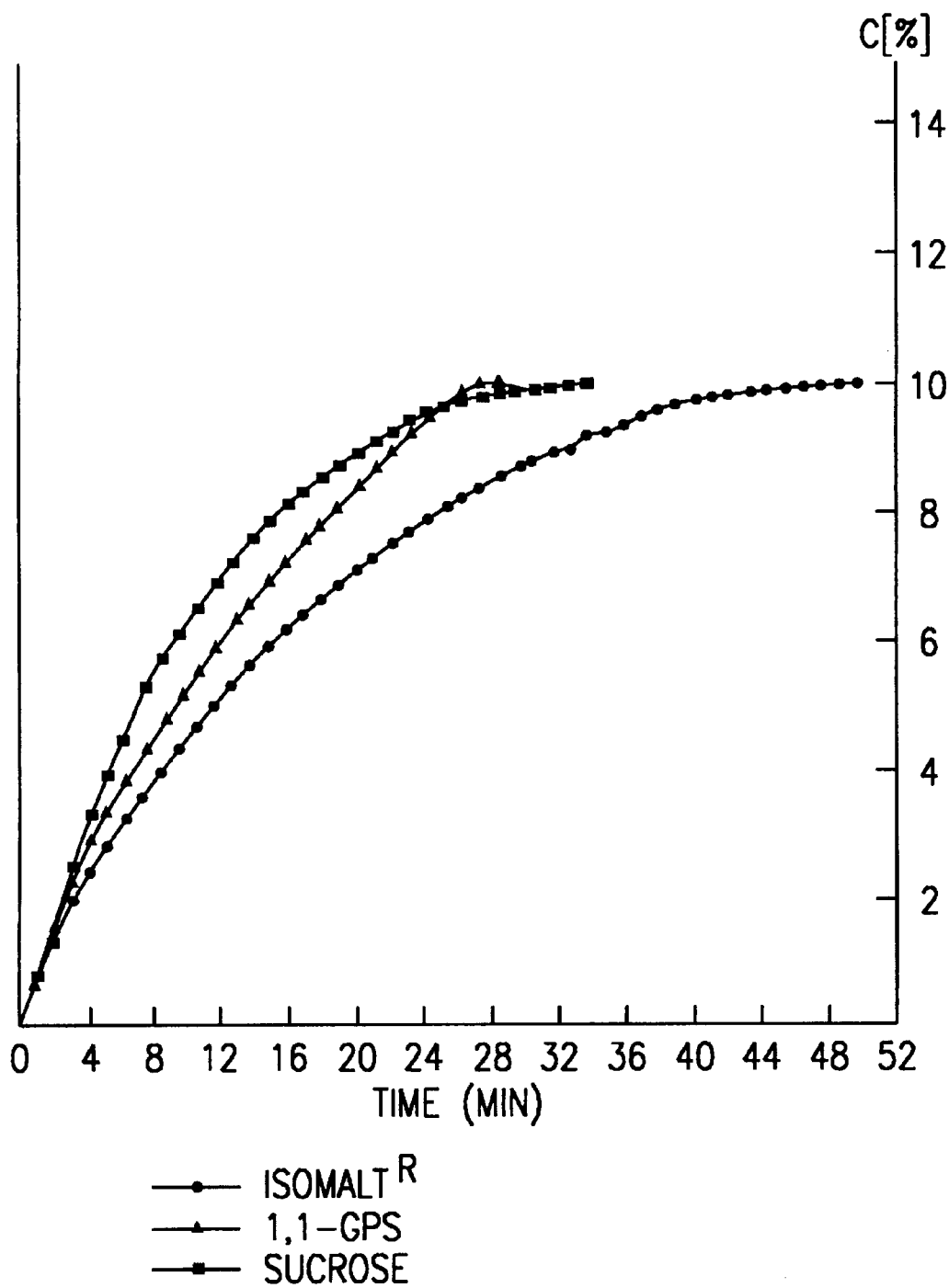

TABLETS CONTAINING A SWEETENING MIXTURE

This application is a 371 of PCT/EP97/04346 filed Aug. 9, 1997.

DESCRIPTION

The present inventions relates to compressed formulations containing a sweetener mixture which comprises 1-O-α-D-glucopyranosil-D-sorbitol. In particular, the invention relates to compressed formulations containing a sweetener mixture composed of 6-O-α-D-glucopyranosil-D-sorbitol, 1-O-α-D-glucopyranosil-D-sorbitol, and 1-O-α-D-glucopyranosil-D-manitol and to the use of these sweetener mixtures in compressed formulations.

Compressed formulations are fancy foods, drugs or also foodstuffs consisting of compacted components. Compressed formulations therefore in general contain a carrier medium or diluting medium, binders, release agents or lubricating jellies, as well as the active ingredients such as flavourings, drugs or sweeteners. Sucrose, lactose, glucose, starch or mannitol are often used as the carrier medium or diluting medium. The use of these carrier or diluting media has the disadvantage that additional binders are required to ensure adequate compressibility.

EP-B1 0 028 905 describes the use of isomaltulose as a diluting medium in pills. But isomalulose has a conparatively low sweetness.

The industrial problem underlying the present invention is to provide compressed formulations which overcome the aforementioned shortcomings and which have particularly improved sweetness, solubility, and compressibility.

The solution of this industrial problem is based on the compressed formulations and containing 1-O-α-D-glucopyranosil-D-sorbitol (abbreviated as 1,1-GPS in what follows), and particularly on compressed formulations containing a sweetener mixture formed by 6-O-α-D-glucopyranosil-D-sorbitol (abbreviated as 1,6-GPS in what follows), 1-O-α-D-glucopyranosil-D-sorbitol, and 1-O-α-D-glucopyranosil-D-mannitol (abbreviated as 1,1-GPM in what follows). Because of their content of 1,1-GPS, particularly because of their content of the sweetener mixture composed of 1,6-GPS, 1,1-GPS, and 1,1-GPM, the compressed formulations of the invention therefore have improved solubility and sweetening power vis-a-vis conventional compressed formulations containing Isomalt® (equimolar mixture of 1,6-GPS and 1,1-GPM, hydrogenated isomaltulose). The compressed formulations according to the invention have the surprising advantage that they can be produced without using binders and that they have improved compressibility, i.e., for obtaining a certain hardness, a comparatively lower compacting pressure is required. Other advantages, associated with the improved compressibility of the inventive compressed formulations, result from their high hardness which is obtained with a comparatively low principal compacting pressure.

Other advantageous embodiments of the invention can be inferred from the dependent claims.

In a preferred embodiment, the invention relates to compressed formulations containing a sweetener mixture of 10 to 50% by weight of 1,6-GPS, 2 to 20% by weight of 1,1-GPS, and 30 to 70% by weight of 1,1-GPM, based on the weight of the sweetener mixture. In another particularly preferred embodiment, the invention relates to compressed formulations containing a sweetener mixture of 5 to 10% by weight of 1,6-GPS, 30 to 40% by weight of 1,1-GPS, and 45 to 60% by weight of 1,1-GPM, based on the weight of the sweetener mixture. Because of the increased 1,1-GPS and the reduced 1,1-GPM content, the latter sweetener mixture imparts to the compressed formulations a further improved sweetening power and solubility in aqueous solutions.

In a particularly preferred embodiment of the invention, the compressed formulations have 50 to 99% by weight of 1,1-GPS or of the sweetener mixture, based on the weight of the compressed formulations. The compressed formulations can contain, in addition, monosaccharides, disaccharides, monosaccharide alcohols, disaccharide alcohols, starch, derivatives of starch, cellulose, derivatives of cellulose, or inulin. The compressed formulations can contain, specifically, sorbitol, mannitol, hydrogenated or non-hydrogenated oligosaccharides, xylitol or sugars, such as sucrose, glucose, fructose or xylose. But these are advantageously present in amounts of less than 30% by weight, preferably less than 5% by weight, based on the weight of the compressed formulations. In a particularly advantageous embodiment, the compressed formulations according to the invention are free of sugar and therefore have a reduced calorific value and are suitable for diabetics.

In a particularly preferred embodiment of the invention, it is provided that the compressed formulations contain, in addition, intense sweeteners such as acesulfame-K, aspartame, cyclamate, glycyrrhizin, thaumatin, saccharin or similar substances. Advantageously, the inventive compressed formulations contain, in addition, flavourings and aromatics such as lemon flavour or peppermint flavour. The inventive compressed formulations can contain food-compatible acids such ascorbic acid or citric acid and, as lubricants, fatty acids or their salts such as magnesium stearate or sodium stearate. Finally, it can be provided that the inventive compressed formulations contain dyes and/or disintegrants such as bicarbonate or carboxymethyl cellulose.

A particularly preferred embodiment provides to produce compressed formulations which transfer pharmaceutically active ingredients into the mouth and throat region and release them there. In the context of the present invention, pharmaceutically active ingredients are understood as substances which have a desired prophylactic or therapeutic effect on the human or animal organism. These substances therefore serve particularly for the prophylaxis or therapy of deficiencies or syndromes. According to the invention, for example enzymes, coenzymes, minerals, vitamins, antibiotics, microbicidal or fungicidal substances such as nicotine, caffeine, eucalyptol, codeine, phenacetin, acetylsalicylic acid, menthol, or other pharmaceutically active ingredients can be incorporated in the compressed formulations. The pharmaceutically active ingredients are to be provided in an amount such that they render the desired pharmaceutical effect. The gentle digestion of the compressed formulations and their peculiar solubility characteristics make the inventive compressed formulations particularly suitable for transferring pharmaceutically active ingredients into the mouth and throat region. Compressed formulations containing Isomalt® as well as sugar-containing compressed formulations dissolve in a comparatively poorer fashion so that the release of the active ingredients is delayed. The release of active ingredients of inventive compressed formulations advantageously begins soon and lasts for an extended period of time.

In a further embodiment, the invention relates to compressed formulations in the form of lozenges or chewable tablets.

Finally, the invention relates to the use of 1,1-GPS or of a sweetener mixture composed of 1,6-GPS, 1,1-GPM and 1,1-GPS in a powder mixture or the compressed formulations made from it for improving its compressibility.

BRIEF DESCRIPTION OF THE DRAWINGS

The following examples and the FIGURE explain details of the invention.

The FIGURE shows graphically the kinetics of the dissolution of inventive and conventional compressed formulations.

EXAMPLE 1

Preparation of lozenges (chewable tablets)

Formula

| | |
|---|---|
| sweetener mixture containing 2% by weignt of 1,1-GPS, 37% by weight of 1,6-GPS, and 53% by weight of 1,1-GPM, based on the weight of the sweetener mixture | 19.54 kg |
| acesulfame-K | 30 g |
| aspartame | 30 g |
| peppermint flavour | 200 g |
| menthol | 100 g |
| magnesium stearate | 100 g |

Preparation

The components are mixed and compacted in a rotary pelleting press of the type Fette P 1200 under the following conditions: compression force: 20 to 70 kN.

A mixture with an increased 1,6-GPS content is preferred for producing the lozenges, and a mixture with increased 1,1-GPM content is used for the production of chewable tablets. No auxiliary agents are required in both cases.

Homogeneously compressed, hard and readily soluble compressed formulations are obtained.

EXAMPLE 2

Kinetics of dissolution of compressed formulations

In order to compare the solubility characteristics of compressed formulations which, according to the invention, contain 1,1-GPS, with compressed formulations containing Isomalt® and sucrose, the kinetics of dissolution of the various compressed formulations were recorded. The compressed formulations containing Isomalt® did not contain 1,1-GPS but had the following composition: 19.54 kg Isomalt®, 200 g peppermint flavour, 100 menthol, 100 g magnesium stearate, 30 g acesulfame-K, 30 g aspartame.

The compressed formulations containing sucrose likewise did not contain 1,1-GPS but had the following composition: 19.6 kg sucrose, 200 g eucalypt-menthol, 100 g menthol, 100 g magnesium stearate.

The inventive compressed formulations containing 1,1-GPS were prepared as in Example 1.

The dissolution characteristics were determined at 37° C. in a solution according to LMBG §35 (Lebensmittel- und Bedarfsmitielgesetz=Food and Auxiliary Media Act). The amounts of solvent and compressed formulations used were chosen so that a 10% solution resulted when the compressed formulations had been completely dissolved. The increase in solution density was determined as a function of time and the concentration expressed in g dry substance per 100 g solution was determined therefrom (see the FIGURE).

The FIGURE shows that the compressed formulations containing 1,1-GPS have a higher solubility than compressed formulations containing Isomalt®. A changed kinetics of dissolution is also obtained vis-a-vis sugar-containing compressed formulations, i.e., compressed formulations containing 1,1-GPS dissolve more rapidly, particularly at the beginning of the dissolution process. The compressed formulations according to the invention therefore advantageously broaden the spectrum of available carrier media, for example for administering drugs.

EXAMPLE 3

Compacting experiments

In order to compare the inventive compressed formulations with compressed formulations prepared from Isomalt® and sucrose in regard to the compacting pressure required for their production and the resulting hardness, the following compacting experiments were made:

The composition of the inventive compressed formulations corresponded to the formula of Example 1.

A mixture of Isomalt® and sucrose with the composition described in Example 2 was used for comparative compressed formulations.

The compacting experiments were carried out with a rotary pelleting press Fette P 1200; the punch was circular and had beveled edges. The punch had a diameter of 20 mm. The rotary pelleting press was equipped with round-rod wheels.

A precompacting pressure of 24.3 kN and a main compacting pressure of 65.4 kN were required for compacting Isomalt®; a compressed formulations with a hardness of 76 N was obtained. A precompacting pressure of 24.0 kN and a main compacting pressure of 65.0 kN was required for compacting sucrose; a compressed formulations with a hardness of 128 N was obtained. By contrast, for compacting the inventive compressed formulations, a precompacting pressure of 28.3 kN and a main compacting pressure of 49.4 kN was required; the resulting compressed formulations had a hardness of 204 N. The compressed formulations according to the invention therefore can be produced with a lower main compacting pressure and harder compressed formulations than in the state of the art are advantageously obtained.

What is claimed is:

1. Compressed formulation, containing 1,1-GPS(1-O-α-D-glucopyranosil-D-sorbitol), wherein said compressed formulation has a minimum hardness of 76 N.

2. Compressed formulation, containing a sweetener mixture composed of 1,6-GPS (6-O-α-D-glucopyranosil-D-sorbitol), 1,1-GPS (1-O-α-D-glucopyranosil-D-sorbitol), and 1,1-GPM (1-O-α-D-glucopyranosil-D-mannitol), wherein said compressed formulation has a minimum hardness of 76 N.

3. The compressed formulation according to claim 2, wherein the sweetener mixture contains 10 to 50% by weight of 1,6-GPS, 2 to 20% by weight of 1,1-GPS, and 30 to 70% by weight of 1,1-GPM, based on the weight of the sweetener mixture.

4. The compressed formulation according to claim 2, wherein the sweetener mixture contains 5 to 10% by weight of 1,6-GPS, 30 to 40% by weight of 1,1-GPS, and 45 to 60% by weight of 1,1-GPM, based on the weight of the sweetener mixture.

5. The compressed formulation according to claim 1, wherein the compressed formulation contains 50 to 99% by weight, based on the weight of the compressed formulation, of 1,1-GPS or sweetener mixture.

6. The compressed formulation according to claim 1, wherein the compressed formulation contains, in addition, a member selected from the group consisting of monosaccharides, disaccharides, monosaccharide/disaccharide alcohols, starch, derivatives of starch, cellulose, derivatives of cellulose, or inulin.

7. The compressed formulation according to claim 1, wherein the compressed formulation contains, in addition, an intense sweetener.

8. The compressed formulation according to claim 1, wherein the compressed formulation contains, in addition, aromatics.

9. The compressed formulation according to claim 1, wherein the compressed formulation contains, in addition, a pharmaceutically active ingredient.

10. The compressed formulation according to claim 1, wherein the compressed formulation has the form of a lozenge.

11. The compressed formulation according to claim 1, wherein the formulation contains in addition excipients selected form the group consisting of dye and disintegrant.

12. The compressed formulation according to claim 7, wherein the intense sweetener is a member selected from the group consisting of acesulfame-K, thaumatin, glycyrrhizin, saccharin and cyclamate.

13. The compressed formulation according to claim 8, wherein the aromatic is selected from the group consisting of fruit and peppermint flavor.

14. The compressed formulation according to claim 9, wherein the pharmaceutically active ingredient is a member selected from the group consisting of enzyme, coenzyme, antibiotic, microbicidal, fungicide, nicotine, caffeine, menthol and eucalyptol.

15. The compressed formulation according to claim 1, wherein the compressed formulation has the form of a chewable tablet.

16. The compressed formulation according to claim 2, wherein the compressed formulation has the form of a lozenge.

17. The compressed formulation according to claim 3, wherein the compressed formulation has the form of a lozenge.

18. The compressed formulation according to claim 4, wherein the compressed formulation has the form of a lozenge.

19. The compressed formulation according to claim 5, wherein the compressed formulation has the form of a lozenge.

* * * * *